United States Patent [19]

McCullough

[11] Patent Number: 4,856,086
[45] Date of Patent: Aug. 8, 1989

[54] RADIO GLASSES

[76] Inventor: Gene McCullough, 2334 W. Van Buren, Apt. 703, Chicago, Ill. 60612

[21] Appl. No.: 123,302

[22] Filed: Nov. 20, 1987

[51] Int. Cl.⁴ .......................... H04B 1/08; H05K 11/00
[52] U.S. Cl. ...................................... 455/344; 455/350; 455/351
[58] Field of Search ............... 455/344, 350, 349, 347, 455/351, 348, 66; D16/103

[56] References Cited

U.S. PATENT DOCUMENTS

D. 212,863  12/1968  Roberts .
2,765,373  10/1956  Smith .................................. 455/344
3,118,145   1/1964  Nee .

FOREIGN PATENT DOCUMENTS 1337289  8/1963  France .................................. 455/351
59-161928  9/1984  Japan ................................... 455/351

OTHER PUBLICATIONS

"Four Eyes... Four Ears"; Mechanics Illustrated; Jun. 1957.

*Primary Examiner*—Robert L. Griffin
*Assistant Examiner*—Ralph E. Smith
*Attorney, Agent, or Firm*—Wood, Dalton, Phillips, Mason & Rowe

[57] ABSTRACT

Radio glasses having an electronic radio receiver integrally mounted in eyeglasses. Earphones are connected to the receiver and removably mounted to the temple of the glasses, said earphones being stored when mounted and adapted for insertion into the wearer's ears for radio use when removed from the temples. Batteries, external switches and tuning and volume controls are all integral with the temples of the glasses.

4 Claims, 1 Drawing Sheet

U.S. Patent    Aug. 8, 1989    4,856,086
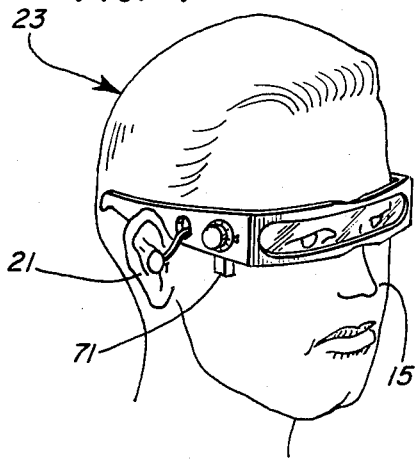
FIG. 1
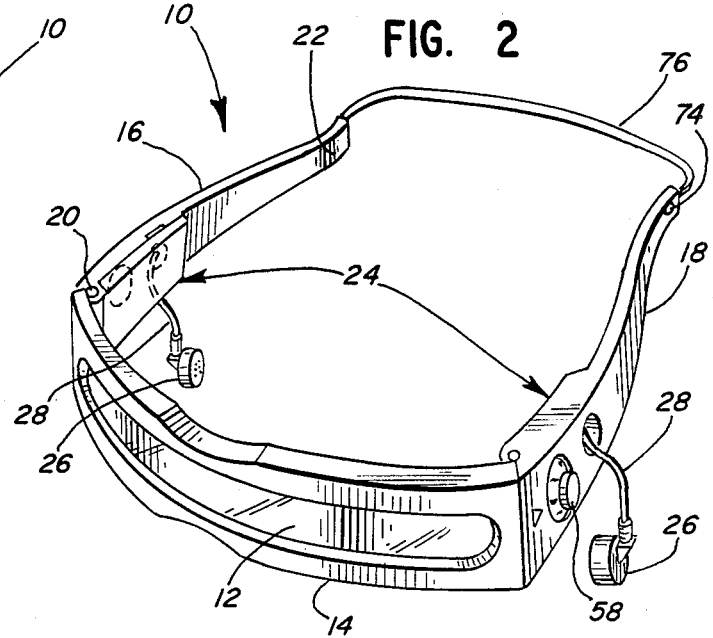
FIG. 2
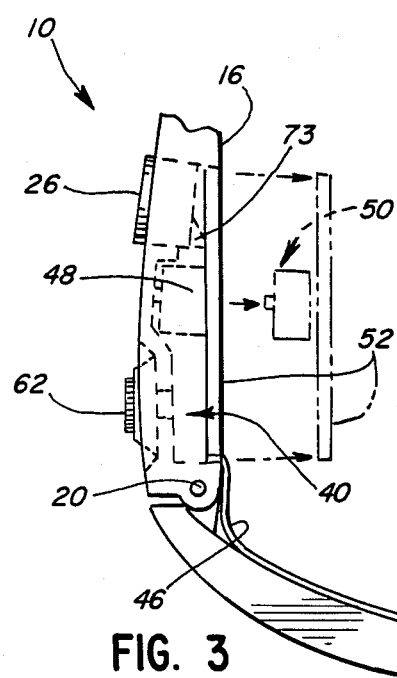
FIG. 3
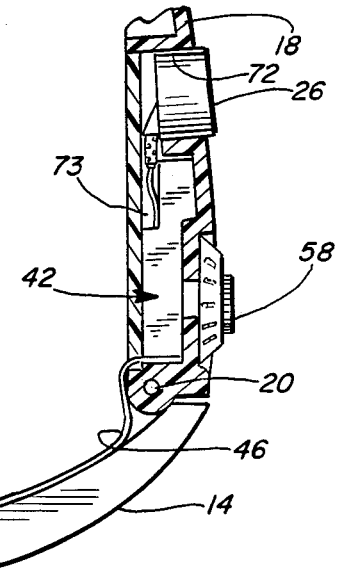
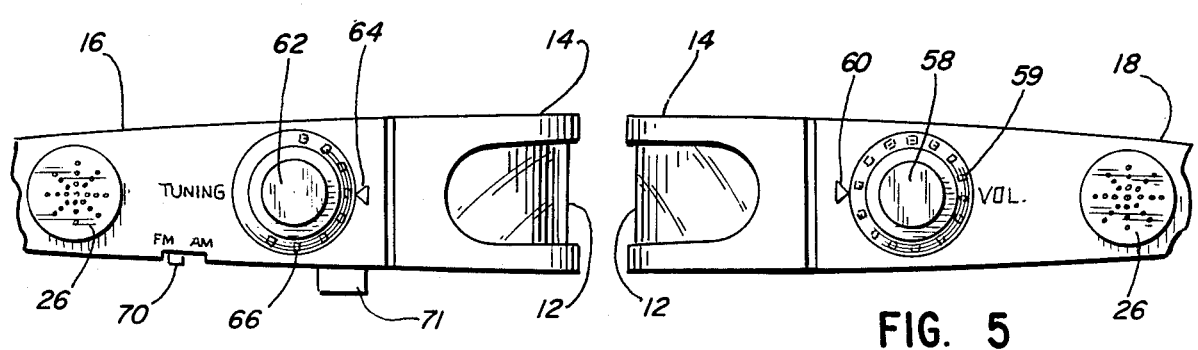
FIG. 4    FIG. 5

RADIO GLASSES

TECHNICAL FIELD

The present invention relates to a receiving device, and more particularly to an electronic receiving device integrally mounted in the temple of a pair of eyeglasses.

BACKGROUND ART

Receiving devices, such as radios, are known in the art. Some portable radios include a small housing containing the electronic circuitry of the radio, and headphones worn on the listener's head to support individual speakers for each ear. These headphones are connected to the radio circuitry by a flexible conductor or wire.

There are numerous problems with this type of radio. In particular, the wire will necessarily hang down from the headphones to the radio with the possibility of becoming entangled with some foreign device. This could cause damage to the radio or headphones, or even injure the listener. Further, when the radio is not being used, the headphones and wire can be difficult to store and can easily become knotted. The headphones can also become uncomfortable after being worn for extended periods of time. Additionally, the headphones and radio are usually physically unattractive on a wearer, and can preclude the wearing of a hat. The headphones can also effect one's hairstyle even after the headphones are removed.

The present invention is directed to overcoming one or more of these problems as set forth above.

SUMMARY OF THE INVENTION

In one aspect of the invention, the device for receiving electrically transmitted signals has a receiving element and converting element which together act to transform the transmitted signal to an audible tone on an earphone. These elements are integrally mounted in the temple of its associated eyewear to provide added comfort and convenience for its user. The earphone is removably mounted in the temple One object of the present invention is to minimize the wires which might become entangled or knotted.

Another object of the present invention is to eliminate the storage problem associated with headphones and their associated wires.

Another object of the present invention is to increase the comfort provided to the wearer while listening to the audio signals.

Another object of the present invention is to provide a more attractive appearance to an individual, both while and after using this device.

Still another object of the present invention is to provide a convenient earphone which can easily be placed in the wearer's ear for use, and aesthetically stored out of the way when not in use.

BRIEF DESCRIPTION OF THE DRAWINGS

FIG. 1 is a perspective view of the preferred embodiment of this invention while in use;

FIG. 2 is a perspective view of the preferred embodiment of this invention with the loud speakers shown removed from the temples;

FIG. 3 is a partial plan view including a cut away view of one of the two temples;

FIG. 4 is a side elevation of the embodiment of FIG. 3; and

FIG. 5 is a side elevation of the embodiment of FIG. 3 opposite that of FIG. 4.

DESCRIPTION OF THE PREFERRED EMBODIMENT

The preferred embodiment of this invention is shown in its common usage in FIG. 1. The radio glasses 10 consist essentially of five basic elements which act together to accomplish the purposes indicated above.

The working relation of these components is better illustrated in FIG. 2. A lens 12, or pair of lenses, which may be, but are not limited to, the type designed to correct vision problems, or alternately act to filter out the sun rays, or both, are mounted in a frame 14. The frame 14 includes an indentation which acts to comfortably support the frame on the bridge of the wearer's nose 14. Temples 16, 18 are hinged mounted on either end of the frame with the pin 20 or screw used as a pivoting point. The temples 16, 18 rest on the ears 21 of the wearer and further include a curved portion 22 which acts to hold the temples against ones head 22 so as to prevent the glasses 10 from falling off.

Included as an integral part of the temples 16, 18 is a receiving unit 24 designed to receive electrically transmitted signals, such as radio waves. This receiving unit may be, but is not limited to, a radio of the AM, FM or AM/FM type (including FM stereo). Electrically connected to the unit 24 are a pair of loud speakers or earphones 26 which in conjunction with the unit 24 convert the received signals to an audio signal which the user can then listen to.

The receiving unit 24 as shown in greater detail in FIGS. 3-5 consists of electronic sections 40, 42 in each of the temples 16, 18 as required. The two electronic sections 40, 42 are electrically connected by appropriate conductors 44 running adjacent to or integral within the frame 14 of the glasses. The conductor 44 includes a slack portion 46 at either end of the frame 14 to allow for flexibility when the temples 16, 18 are pivoted at their hinges. This conductor 44 further may act as an antenna for the receiving unit 24.

To provide power to the receiving unit 24 and speakers (or earphones) 26, a space 48 is provided for batteries 50 to be mounted. A plate 52 is included to hold the batteries 50 in place. The plate 52 is removably attached to the temple 16 by, for example, a suitable snap connection, enabling the batteries 50 to be replaced and further providing access to the unit's electronic components, which are not shown in detail. The plate 52 is shown in phantom in FIG. 3 in its removed position.

The unit 24 also includes a rotary volume control 58 with appropriate indications 59 thereon to control the level of the audio signal. A marker 60 for indicating the present setting of the volume control 58 is fixed on the temple 18. This volume control 58 may include an ON/OFF switch built in, or alternately a separate ON/OFF switch may be provided in the temple 18.

A rotary tuning control 62 is mounted in the temple 16 opposite that of the volume control 58. The tuning control 62 has appropriate indications 64 of channel selections, again with a marker 66 provided to show the present selected channel. In the AM/FM type radio illustrated, a switch 70 is included to select the appropriate frequency band. If desired, the temple 16 may be secured to the frame 14 by a suitable snap-away connector to change tuning controls (for example, from AM to FM stereo).

A suitably padded balancer 71 may also be provided on the underside of a temple 16 to stabilize the glasses 10 when one of the controls 58, 62 is turned. Specifically, the balancer 71 may be pivotably mounted so that it may be either positioned to engage the wearer's cheekbone to stabilize the glasses 10 or positioned spaced from the cheekbone to avoid irritation when the controls 58, 62 are not being changed.

In the preferred embodiment the earphones 26 are removably mounted. In FIGS. 3–5 the earphones 26 are shown mounted in the temples 16, 18, and in FIGS. 1 and 2 are shown in their removed position. When the earphones 26 are removed from the temples 16, 18 they remain connected to the receiving unit 24 via electrical conductors 28. These conductors 28 could also be used to act as an antenna for the unit 24. When removed, the earphones 26 may be inserted in the wearer's ears 21 as indicated in FIG. 1. Optionally, the wearer can insert one earphone 26 in one ear while leaving the other in its associated temple to enable the wearer to hear outside noises easier.

When mounted in the temples 16, 18, the earphones 26 are suitably secured against falling out by, for example, frictional engagement with the temples 16, 18. This may be accomplished by providing a recess or opening 72 in the temples 16, 18 which is substantially in the shape of the earphone 26, but slightly smaller at one spot so as to bind against the earphone 26. In addition, the recess 72 should be such as to allow the earphone to be disposed substantially flush to the sides of the temples 16, 18 but with a small portion extending out so that the earphone may be easily grasped and removed by the wearer (see FIG. 3).

In order to store the conductors 28 when the earphones 26 are so mounted, a suitable recess 73 is also provided in each temple 16, 18 into which the conductors 28 can be inserted. The glasses 10 thus can be worn even when not used as a radio and will still provide an attractive appearance.

In the preferred embodiment, clips or snaps 74 are provided at the unhinged end of each temple 16, 18 to which a strap or band 76 may be attached. This strap 76 allows the wearer to wear the radio glasses around his or her neck and continue to hear the sounds from the earphones. Radio glasses with sunglass lens could then be used at night.

As indicated above the present invention provides solutions to problems resident in the prior art. With the electronic sections 40, 42 of the unit 24 integrally mounted in the temples 16, 18 and the earphones 26 removably mounted on short conductors 28, the problems associated with tangled and knotted wires are virtually eliminated. Further, these radio glasses 10 can be folded up and put in a case for storage without having to worry about wires or headphones. Still further, while being worn the radio glasses 10 are similar in comfort and aesthetically pleasing appearance to an ordinary pair of eyeglasses. Likewise, after being removed the radio glasses will not leave an impression in the wearer's hair as do headphones.

Other aspects, objects and advantages of this invention can be obtained from a study of the drawings, the disclosure and the appended claims.

I claim:

1. A device worn about ones head for receiving electrically transmitted signals, comprising:
   a lens for aiding in vision;
   a frame for holding said lens;
   first and second temples hinged to said frame on opposite ends for supporting said frame;
   a radio integrally mounted in one of said temples;
   first and second loud speakers electrically connected to said radio; and
   recesses within opposite temples for removably mounting said loud speakers within opposite temples;
   wherein each recess stores the electrical connections for said loud speakers when mounted, and said loud speakers securely fit in a wearer's ear for listening when removed from said recesses.

2. A device worn about ones head for receiving electrically transmitted signals, comprising:
   a lens for aiding in vision;
   a frame for holding said lens;
   first and second temples hinged to said frame on opposite ends for supporting said frame;
   a radio integrally mounted in one of said temples;
   first and second loud speakers electrically connected to said radio, said loud speakers securely fitting in a wearer's ear for listening when removed from said mounting means; and
   recesses within opposite temples for removably mounting said loud speakers within opposite temples;
   wherein said speakers are substantially flush with the temple sides when mounted, and said loud speakers securely fit in a wearer's ear for listening when removed from said recesses.

3. A device worn about ones head for receiving electrically transmitted signals, comprising:
   a lens for aiding in vision;
   a frame for holding said lens;
   first and second temples hinged to said frame on opposite ends for supporting said frame, each of said temples having a recess therein;
   a radio integrally mounted in one of said temples;
   first and second loud speakers;
   first and second conductors connecting said first and second loud speakers respectively to said ratio and storable in the recesses in said temples; and
   means for frictionally holding the loud speakers in the temple recesses;
   wherein said speakers are substantially flush with the temple sides when mounted and said speakers when mounted further have a graspable portion permitting manual removal.

4. A device worn about ones head for receiving electrically transmitted signals, comprising:
   a lens for aiding in vision;
   a frame for holding said lens;
   first and second temples hinged to said frame on opposite ends for supporting said frame, each of said temples having a recess therein;
   a radio integrally mounted in one of said temples;
   first and second loud speakers;
   first and second conductors connecting said first and second loud speakers respectively to said radio and storable in the recesses in said temples;
   means for frictionally holding the loud speakers in the temple recesses; and
   a balancer secured to one of said temples to stabilize the device by engaging a wearer's cheekbone;
   wherein said speakers when mounted further having a graspable portion permitting manual removal.

* * * * *